United States Patent [19]

Pastor et al.

[11] Patent Number: 4,835,202

[45] Date of Patent: May 30, 1989

[54] (HYDROXYPHENYL) PHOSPHINE STABILIZED COMPOSITIONS

[75] Inventors: Stephen D. Pastor, Basel, Switzerland; John D. Spivack, Spring Valley; Edward T. Hessell, Rochester, both of N.Y.

[73] Assignee: Ciba-Geigy Corporation, Ardsley, N.Y.

[21] Appl. No.: 123,469

[22] Filed: Nov. 20, 1987

[51] Int. Cl.$^4$ .......................... C08K 5/50; C07D 9/02
[52] U.S. Cl. ...................................... 524/154; 568/17; 252/400.29
[58] Field of Search .................... 252/400.24; 524/154; 568/17

[56] References Cited

U.S. PATENT DOCUMENTS

| | | | |
|---|---|---|---|
| 2,981,716 | 4/1961 | Street et al. | 524/154 |
| 3,055,861 | 9/1962 | Hersh et al. | 524/154 |
| 3,261,871 | 7/1966 | Fritzsche et al. | 568/17 |
| 3,402,196 | 9/1968 | Dannels et al. | 260/502.4 |
| 3,754,019 | 8/1973 | Sarett et al. | 560/141 |
| 4,008,282 | 2/1977 | Townsend et al. | 568/17 |
| 4,411,985 | 10/1983 | Morrow et al. | 430/352 |
| 4,439,570 | 3/1984 | Messina et al. | 524/154 |
| 4,540,823 | 9/1985 | Doorakian et al. | 568/10 |
| 4,593,128 | 6/1986 | Hinney et al. | 524/154 |

FOREIGN PATENT DOCUMENTS 1193942  6/1965  Fed. Rep. of Germany ........ 568/17
1025570  4/1966  United Kingdom .................. 568/17

OTHER PUBLICATIONS

Tetrahedron, vol. 25, pp. 5623-5637 (1969).
Sinear et al., Derivatives of Triphenylphosphine, pp. 2001-2006, vol. 25, (1960), Liebigs Ann. Chem. 658, pp. 103-112 (1962).
Recl. Trav. Chim. Pays-Bas 102, pp. 326-330, (1983).

Primary Examiner—John Kight
Assistant Examiner—Kriellion Morgan
Attorney, Agent, or Firm—Harry Falber

[57] ABSTRACT (Hydroxyphenyl)phosphine derivatives of the formula

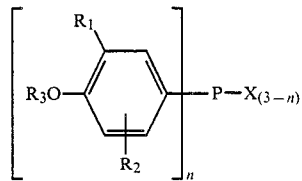

are effective in stabilizing organic materials against oxidative, thermal and actinic degradation, said derivatives being particularly effective as process stabilizers in organic materials containing phenolic antioxidants.

28 Claims, No Drawings

(HYDROXYPHENYL) PHOSPHINE STABILIZED COMPOSITIONS

Organic polymeric materials such as plastics and resins are subject to thermal, oxidative and photodegradation. A great variety of stabilizers are known in the art for stabilizing a diversity of substrates. Their effectiveness varies depending upon the causes of degradation and the substrate stabilized. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Various (hydroxyphenyl)phosphines have been disclosed in the prior art. For example, U.S. Pat. No. 3,402,196 discloses 3,5-di-alkyl-4-hydroxyphenylphosphonic and phosphinic acids as stabilizers against oxidation in organic materials such as lubricants, hydrocarbon fuels, and plastics. The compounds of this patent are pentavalent phosphorus esters. Ortho-unsubstituted hydroxyphenylphosphines are also disclosed in U.S. Pat. No. 3,754,019. U.S. Pat. No. 4,411,985 describes unsubstituted 4-(hydroxyphenyl)phosphines as stabilizer precursors for photographic silver halide materials. U.S. Pat. No. 4,540,823 discloses unsubstituted 4-(hydroxyphenyl)phosphonium salts as initiators for epoxide polymerization.

P-(3,5-di-tert-butyl-4-hydroxyphenyl)diphenylphosphine is disclosed by Müller et al. in *Liebigs Ann. Chem.*, 658, 103 (1962). Finally, the synthesis of unsubstituted 4-(hydroxyphenyl)phosphines is disclosed in (a) Senear et al., *J. Org. Chem.* 25, 2001 (1960), (b) Tsvetkov et al., *Tetrahedron* 25, 5623 (1969), and (c) van Zon et al., *Recl. Trav. Chim. Pays*-Bas 102, 326 (1983).

It has now been determined that the compositions of this invention exhibit a variety of desirable properties stemming from the presence therein of the indicated phosphine stabilizers. Thus, the compounds serve to protect various substrates such as polyolefins, elastomers and lubricating oils against the adverse effects of oxidative and thermal degradation. They are most effective as process stabilizers in polyolefin compositions which may contain metal salts of fatty acids and which also contain a phenolic antioxidant. Thus, they serve to substantially reduce color formation resulting from the presence of the phenolic antioxidant and/or from the processing conditions as well as to directly protect the polymer from said processing conditions.

It is the primary object of this invention to provide compositions of organic materials stabilized against oxidative, thermal and actinic degradation by the presence therein of a class of phosphine derivatives.

It is a further object to provide a class of novel phosphine derivatives which exhibits a broad range of improved stabilization performance characteristics.

Various other objects and advantages of this invention will become evident from the following description thereof.

The compounds utilized in the compositions of this invention correspond to the formula

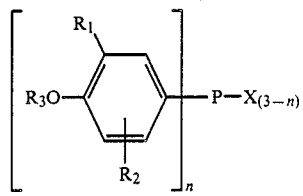

wherein n is an integer from 1–3;

$R_1$, $R_2$ and X are independently hydrogen, $C_1$–$C_{18}$ alkyl, $C_5$–$C_{12}$ cycloalkyl, phenyl, phenyl substituted by alkyl of 1 to 18 carbon atoms, $C_7$–$C_9$ aralkyl or said aralkyl substituted by alkyl of 1 to 18 carbon atoms; and $R_3$ is hydrogen or —Si($R_4$)($R_5$)($R_6$) with $R_4$, $R_5$ and $R_6$ being independently $C_1$–$C_4$ alkyl or phenyl.

Preferred compounds within the above structure are those wherein both $R_1$ and $R_2$ are in the ortho position to the $OR_3$ group. The $R_1$ and $R_2$ groups are preferably straight-chain or branched alkyl with 1 to 8 carbon atoms, such as methyl, n-butyl, sec-butyl, tert-butyl, tert-pentyl, 2-ethylhexyl, n-octyl and 1,1,3,3-tetramethylbutyl. The groups methyl, tert-butyl, tert-pentyl and 1,1,3,3-tetramethylbutyl are especially preferred. Also especially preferred, as previously noted, is for the $R_2$ group to be in the ortho position to the $OR_3$ group, particularly if $R_2$ is tert-alkyl.

When $R_1$, $R_2$ and X are cycloalkyl, they include cyclopentyl or cyclohexyl and when they are aralkyl, they represent benzyl, alpha-methylbenzyl or alpha, alpha-dimethylbenzyl.

Other preferred substituents are X as methyl or phenyl and $R_3$ as hydrogen or trimethylsilyl.

The derivatives of this invention wherein $R_3$ is the silylated radical can be prepared by reacting the appropriately substituted brominated silane of the formula

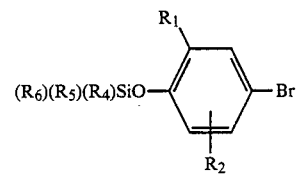

with the appropriately substituted halophosphine in a solvent to yield the desired product. Typical halophosphines include diphenylchlorophosphine, dichlorophenylphosphine, methyldichlorophosphine, tert-butyldichlorophosphine, phosphorus trichloride, among others. The solvent is preferably a heterocyclic ether such as tetrahydrofuran. The reaction temperature ranges from −78° C. to 30° C. The reaction is also conducted in the presence of an organometallic base such as n-butyllithium, tert-butyllithium or sec-butyllithium or n-butyllithium plus N,N,N′,N′-tetramethylethylenediamine. Corresponding organometallic bases of sodium or potassium are also contemplated as useful for this purpose.

The corresponding hydroxyphenyl-phosphines can be prepared by hydrolyzing the above noted product utilizing silane deprotecting agents such as tetrabutylammonium fluoride trihydrate, dilute sodium hydroxide solution, methanol or methanol and water heated to reflux. This reaction is likewise conducted in a solvent such as tetrahydrofuran. The starting materials needed to prepare the stabilizers of this invention are items of commerce or can be prepared by known methods.

Certain of the aforementioned derivatives are novel and thus also form part of the invention. These derivatives correspond to the above noted formula wherein $R_1$, $R_2$ and X are as previously defined, when n is 1, $R_3$ is —$Si(R_4)(R_5)(R_6)$ with $R_4$, $R_5$ and $R_6$ as previously defined, and when n is 2 or 3, $R_3$ is a previously defined. The various preferred embodiments equally apply.

The phenolic compounds of the present invention are particularly effective in stabilizing organic materials subject to oxidative, thermal and actinic degradation, such as plastics, polymers and resins. The silyl ethers are valuable intermediates in the preparation of such compounds.

Substrates in which these compounds are particularly useful are polyolefins such as polyethylene and polypropylene; polystyrene, including impact polystyrene, ABS resin, SBR, isoprene, as well as natural rubber, polyesters including polyethylene terephthalate and polybutylene terephthalate, including copolymers, and lubricating oils such as those derived from mineral oil.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under (1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.
8. Polymers which are derived from $\alpha,\beta$-unsaturated acids and derivatives thereof, such as polyacrylates and polymethacrylates, polyacrylamide and polyacrylonitrile.
9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl-butyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-timethylhexamethylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.

In general, the compounds of the present invention are employed in from about 0.01 to about 5% by weight of the stabilized composition, although this will vary with the particular substrate and application. As advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. ANTIOXIDANTS 1.1. Alkylated monophenols, for example
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example
2,6-di-tert.butyl-4-methoxyphenol
2,5-di-trt.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkylidene-bisphenols, for example
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrate]
di-(3-tert.butyl-4-hydroxy-5-methylphenyl)-dicyclopentadiene
di-[2-(3'-tert.butyl-2'-hydroxy-5'-methyl-benzyl)-6-tert.-butyl-4-methylphenyl]-terephthalate.

1.5. Benzyl compounds, for example
1,3,5-tri-(3,5-di-tert.butyl-4-hydroxybenzyl)-2,4,6-trimethylbenzene-di-(3,5-di-tert.butyl-4-hydroxybenzyl)-sulfide
3,5-di-tert.butyl-4-hydroxybenzyl-mercapto-acetic acid isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid-diocta-decyl ester
3,5-di-tert.butyl-4-hydroxybenzyl-phosphoric acid-monoethyl ester, calcium-salt 1.6. Acylaminophenols, for example
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate 1.7. Esters of β-(3,5-di-tert.butyl-4-hydroxyphenyl)-propionic acid with monohydric or polyhydric alcohols, for example 1.8. Esters of β-(5-tert-butyl-4-hydroxy-3-methylphenyl)-propionic acid with monohydric or polyhydric alcohols, for example

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.9. Amides of β-(3,5-di-tert.butyl-4-hydroxyphenyl)-propionic acid for example
N,N'-di-(3,5-di-tert.butyl-4-hydroxyphenylpropionyl)-hexamethylenediamine
N,N'-di-(3,5-di-tert.butyl-4-hydroxyphenylpropionyl)-trimethylenediamine
N,N'-di-(3,5-di-tert.butyl-4-hydroxyphenylpropionyl)-hydrazine

2. UV ABSORBERS AND LIGHT STABILIZERS 2.1. 2-(2'-Hydroxyphenyl)-benzotriazoles, for example, the 5'-methyl-, 3',5'-di-tert.butyl-, 5'-tert.butyl-, 5'-(1,1,3,3-tetramethylbutyl)-, 5-chloro-3',5'-di-tert.-butyl-, 5-chloro-3'-tert.butyl-5'-methyl-, 3'-sec.butyl-5'-tert.butyl-, 4'-octoxy, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Esters of optionally substituted benzoic acids for example, phenyl salicylate, 4-tert.butyl-phenylsalicylate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyano-vinyl)-2-methylindoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclo-hexyl-di-ethanolamine, nickel dibutyldithiocarbamate, nickel salts of 4-hydroxy-3,5-di-tert.-butylbenzylphosphonic acid monoalkyl esters, such as of the methyl, ethyl or butyl ester, nickel complexes of ketoximes such as of 2-hydroxy-4-methylphenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate, bis-(1,2,2,6,6-pentamethylpiperidyl)-sebacate, n-butyl-3,5-di-tert.butyl-4-hydroxybenzyl malonic acid bis-(1,2,2,6,6-pentametylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylenediamine and 4-tert.octylamino-2,6-dichloro-1,3,5-s-triazine, tris(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-di-octyloxyoxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis(3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-.butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert.butylphenyl)-phosphite, di-isodecylpentaerythritol diphosphite, di-(2,4-di-tert.-butylphenyl)pentaerythritol diphosphite, tristearylsorbitol triphosphite, tetrakis-(2,4-di-tert.butylphenyl)-4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithio-carbamate, dioctadecyldisulfide, pentaerythritol-tetrakis-(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinyl-pyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearyl-thiodipropionate.

Still another group of coadditives which can be advantageously used in conjunction with the instant (hydroxyphenyl)phosphines are the hydroxylamines such as N,N-dialkylhydroxylamines and the N,N-diaralkylhydroxylamines. Examples of such hydroxylamines include the N,N-dialkylhydroxylamines with alkyl of 1 to 18 carbon atoms, preferably alkyl of 8 to 18 carbon atoms; and N,N-dibenzylhydroxylamine and substituted N,N-dibenzylhydroxylamines where the benzyl moiety is substituted by alkyl of 1 to 12 carbon atoms or by alpha,alpha-dimethyl-benzyl.

While the instant phosphines can be beneficially used as stabilizers for a variety of substrates, particularly the polyolefins, both alone and in conjunction with other coadditives, the introduction of the instant phosphines into polyolefins, optionally containing various alkali metal, alkaline earth metal and aluminum salts of higher fatty acids (see Additive #7 hereinabove), with hindered phenolic antioxidants results in enhanced and particularly salubrious protection to such substrates in terms of reducing color formation stemming from the presence of the phenols. Such phenolic antioxidants include n-octadecyl 3,5-di-tert-butyl-4-hydroxyhydrocinnamate, neopentane-tetrayl tetrakis-(3,5-di-tert-butyl-4-hydroxy-hydrocinnamate), di-n-octadecyl 3,5-di-tert-butyl-4-hydroxybenzyl-phosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-di-oxaocta-methylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-di-methyl-4-tert-butyl-3-hydroxybenzyl)-isocyanurate, 1,1,3-tris-(2-methyl-4-hydroxy-5-tert-butylphenyl)butane, 1,3,5-tris-[2-(3,5-di-tert-butyl-4-hydroxy-hydrocinnamoyloxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis-[2-(3,5-tert-butyl-4-hydroxyhydroxo-cinnamoyloxy)-ethyl]-oxamide, and preferably neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-(3,5-di-tert-butyl-4-hydroxybenzyl)isocyanurate, 2,6-di-tert-butyl-p-cresol or 2,2'-ethylidene-bis(4,6-di-tert-butylphenol).

Likewise, the instant compounds prevent color formation when hindered amine light stabilizers are present, such hindered amines including bis(1,2,2,6,6-pentamethyl-4-piperidyl)-2-n-butyl-2-(3,5-di-tert-butyl-4-hydroxybenzyl)malonate; bis(2,2,6,6-tetramethyl-4-piperidyl)sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

The following examples illustrate the embodiments of this invention. In these examples, all parts given are by weight unless otherwise specified.

EXAMPLE 1

(3,5-Di-tert-butyl-4-trimethylsilyloxyphenyl)diphenylphosphine

A stirred suspension of 20.0 g (56 mmol) of 4-bromo-2,6-di-tert-butylphenoxy(trimethyl)silane in 80 ml of dry tetrahydrofuran at $-78°$ C. is admixed dropwise with 38 ml (56 mmol) of a 1.55M solution of n-butyllithium in hexane. The resulting homogeneous solution is stirred for 1 hour at $-78°$ C. and then 12.36 g (56 mmol) of diphenylchlorophosphine is added dropwise. The reaction mixture is stirred for 24 hours at room temperature, and then the suspension of lithium chloride is removed by filtration. The solvent is removed in vacuo. The residue is dissolved in 250 ml of diethyl ether and extracted (3×250 ml) with water. The organic phase is dried over anhydrous sodium sulfate and evaporated in vacuo to give 27.8 grams of a yellow liquid. The crude product is purified by preparative HPLC (silica gel, 99:1 heptane:ethyl acetate eluent) to give 10.7 grams (41%) of a white solid, m.p. 76°–80° C.

Anal. Calcd for $C_{29}H_{39}OPSi$: C, 75.3; H, 8.5. Found: C, 75.5; H, 8.6.

EXAMPLE 2

Bis(3,5-di-tert-butyl-4-trimethylsilyloxphenyl)phenylphosphine

The method of Example 1 is used to prepare bis(3,5-di-tert-butyl-4-trimethylsilyloxyphenyl)phenylphosphine from 20.0 g (56 mmol) of 4-bromo-2,6-di-tert-butylphenoxy-(trimethyl)silane, 35 ml (56 mmol) of 1.6M n-butyllithium in hexane and 5.01 g (28 mmol) of dichlorophenylphosphine. After the solvent is removed in vacuo, the residue is dissolved in 250 ml of diethylether and filtered to remove lithium chloride. The filtrate is concentrated in vacuo and the crude product purified by preparative HPLC (silica gel, 99:1 heptane:ethyl/acetate eluent) followed by recrystallization from methanol to give 7.2 grams (29%) of a white solid, m.p. 129°–131° C.

Anal. Calcd for $C_{40}H_{63}O_2PSi_2$: C, 72.5; H, 9.6. Found: C, 72.4; H, 9.9.

EXAMPLE 3

Tris(3,5-di-tert-butyl-4-trimethylsilyloxy)phosphine

The method of Example 1 is utilized to prepare tris-(3,5-di-tert-butyl-4-trimethylsilyloxy)phosphine using 20.0 g (56 mmol) of 4-bromo-2,6-di-tert-butylphenoxy(trimethyl)-silane, 35 ml (56 mmol) of a 1.6M solution of n-butyllithium in hexane, and 2.56 g (18.7 mmol) of phosphorus trichloride. The solvent is removed in vacuo. The residue is dissolved in 250 ml of diethyl ether and filtered to remove lithium chloride. The filtrate is concentrated in vacuo and the residue triturated in acetonitrile to give 6.1 g (38%) of a white solid, m.p. 168°–170° C.

Anal. Calcd for $C_{51}H_{87}O_3PSi_3$: C, 70.9; H, 10.2. Found: C, 71.0; H, 10.6.

EXAMPLE 4

(3,5-Di-tert-butyl-4-hydroxyphenyl)diphenylphosphine 3,5-Di-tert-butyl-4-hydroxyphenyl(diphenyl)phosphine is isolated by preparative HPLC (silica gel, 99:1 heptane:ethyl/acetate efluent) during the purification of the compound of Example 1 as a white solid (6.5 g): m.p. 92°–93° C.

Anal. Calcd for $C_{26}H_{31}OP$: C, 80.00; H, 8.0. Found: C, 79.8; H, 8.1.

EXAMPLE 5

Bis(3,5-di-tert-butyl-4-hydroxyphenyl)phenylphosphine

A solution of 1.0 g (1.5 mmol) of bis(3,5-di-tert-butyl-4-trimethylsilyloxyphenyl)phenylphosphine and 2.0 g of water in 25 ml of methanol is heated at reflux temperature for 4 hours. The solvent is removed in vacuo and the residue purified by flash chromatography (silica gel, 9:1 heptane:ethyl/acetate eluent) to give 0.3 g (34%) of a white solid, m.p. 138°–140° C.

Anal. Calcd for $C_{34}H_{47}O_2P$: C, 78.7; H, 9.1. Found: C, 78.3; H, 9.1.

EXAMPLE 6

Tris(3,5-di-tert-butyl-4-hydroxyphenyl)phosphine

A solution of 5.0 g (5.8 mmol) of tris(3,5-di-tert-butyl-4-trimethylsilyloxyphenyl)phosphine and 4.0 ml of water in 100 ml of methanol is heated at reflux temperature for 48 hours. The solvent is removed in vacuo from the reaction mixture and the residue is recrystallized from nitromethane. The mass spectrum shows a molecular ion at m/z=646.

EXAMPLE 7

This example illustrates the thermal stabilizing effectiveness of the instant stabilizers alone or in combination with a phenolic antioxidant in polypropylene.

| Base | Formulation |
|---|---|
| Polypropylene* | 100 parts |
| Calcium Stearate | 0.10 parts |

*Profax 6501 from Himont

Stabilizers are solvent blended into polypropylene as solutions in methylene chloride and after removal of the solvent by evaporation at reduced pressure, the resin is extruded using the following extruder conditions:

| | Temperature (°C.) |
|---|---|
| Cylinder #1 | 232 |
| Cylinder #2 | 246 |
| Cylinder #3 | 260 |
| Die #1 | 260 |
| Die #2 | 260 |
| Die #3 | 260 |
| RPM | 100 |

The melt flow rate (MFR) is determined by ASTM method 1238 condition L. The melt flow rate is a measure of the molecular weight for a specific type of polymer. Correspondingly, specimen yellowness index is determined according to ASTM D1925. The results are shown below.

| Additive | Conc. (% by wt.) | MFR (g/10 min.) After Extrusion | | YI Color After Extrusion | | |
|---|---|---|---|---|---|---|
| | | 1 | 5 | 1 | 3 | 5 |
| None | — | 4.4 | 11.5 | 3.6 | 3.9 | 4.6 |
| AO 1[(1)] | 0.1 | 2.5 | 4.2 | 6.1 | 7.9 | 9.4 |
| Compound of Example 4 | 0.1 | 1.6 | 2.0 | 2.9 | 4.2 | 5.0 |
| Compound of Example 4 with 0.05% of AO1 | 0.1 | 1.6 | 2.1 | 2.0 | 4.1 | 4.7 |

[(1)]AO 1 is neopentanetetrayl tetrakis[3-(3',5'-di-tert-butyl-4'-hydroxyphenyl) propionate]

Summarizing, it is seen that this invention provides organic materials stabilized against degradation by the presence therein of various novel phosphines. Variations may be made in proportions, procedures and materials without departing from the scope of the invention as defined by the following claims.

What is claimed is:

1. A composition of matter comprising a polymer, plastic or lubricating oil subject to oxidative, thermal or actinic degradation stabilized with an effective stabilizing amount of a compound of the formula

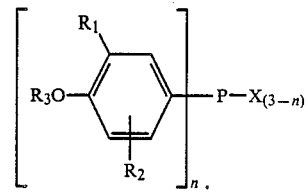

wherein
n is an integer from 1–3;
$R_1$, $R_2$ and X are independently hydrogen, $C_1$–$C_{18}$ alkyl, $C_5$–$C_{12}$ cycloalkyl, phenyl, phenyl substituted by alkyl of 1 to 18 carbon atoms, $C_7$–$C_9$ aralkyl or said aralkyl substituted by alkyl of 1 to 18 carbon atoms; and
$R_3$ is hydrogen or —$Si(R_4)(R_5)(R_6)$ with $R_4$, $R_5$ and $R_6$ being independently $C_1$–$C_4$ alkyl or phenyl.

2. The composition of claim 1, wherein $R_1$ and $R_2$ are alkyl of from 1 to 8 carbon atoms.

3. The composition of claim 2, wherein $R_1$ and $R_2$ are tert-butyl.

4. The composition of claim 1, wherein $R_2$ is in the ortho position to the $OR_3$ group.

5. The composition of claim 1, wherein X is methyl or phenyl.

6. The composition of claim 1, wherein $R_3$ is hydrogen or trimethylsilyl.

7. The composition of claim 1, containing (3,5-di-tert-butyl-4-trimethylsilyloxyphenyl)diphenylphosphine.

8. The composition of claim 1, containing bis(3,5-di-tert-butyl-4-trimethylsilyloxyphenyl)phenylphosphine.

9. The composition of claim 1, containing tris(3,5-di-tert-butyl-4-trimethylsilyloxy)phosphine.

10. The composition of claim 1, containing (3,5-di-tert-butyl-4-hydroxyphenyl)diphenylphosphine.

11. The composition of claim 1, containing bis(3,5-di-tert-butyl-4-hydroxyphenyl)phenylphosphine.

12. The composition of claim 1, containing tris(3,5-di-tert-butyl-4-hydroxyphenyl)phosphine.

13. The composition of claim 1, wherein the polymer is a synthetic polymer.

14. The composition of claim 13, wherein the synthetic polymer is a polyolefin homopolymer or copolymer.

15. The composition of claim 1 which also contains a phenolic antioxidant.

16. A method for stabilizing a polymer, plastic or lubricating oil against oxidative, thermal and actinic degradation which comprises incorporating into said polymer, plastic or lubricating oil an effective stabilizing amount of a compound of claim 1.

17. A compound of the formula

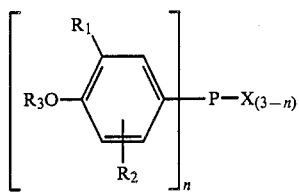

wherein
$R_1$, $R_2$ and X are independently hydrogen, $C_1$–$C_{18}$ alkyl, $C_5$–$C_{12}$ cycloalkyl, phenyl, phenyl substituted by alkyl of 1 to 18 carbon atoms, $C_7$–$C_9$ aralkyl or said aralkyl substituted by alkyl of 1 to 18 carbon atoms;
n is 1–3;
when n=1, $R_3$ is —Si($R_4$)($R_5$)($R_6$) with $R_4$, $R_5$ and $R_6$ being independently $C_1$–$C_4$ alkyl or phenyl; and
when n=2 or 3, $R_3$ is hydrogen or —Si($R_4$)($R_5$)($R_6$).

18. The compound of claim 17, wherein $R_1$ and $R_2$ are alkyl of from 1 to 8 carbon atoms.

19. The compound of claim 18, wherein $R_1$ and $R_2$ are tert-butyl.

20. The compound of claim 17, wherein $R_2$ is in the ortho position to the $OR_3$ group.

21. The compound of claim 17, wherein X is methyl or phenyl.

22. The compound of claim 17, wherein n is 1 and $R_3$ is trimethylsilyl.

23. The compound of claim 17, wherein n is 2 or 3 and $R_3$ is hydrogen or trimethylsilyl.

24. (3,5-Di-tert-butyl-4-trimethylsilyloxyphenyl)-diphenylphosphine according to claim 22.

25. Bis(3,5-di-tert-butyl-4-trimethylsilyloxyphenyl)-phenylphosphine according to claim 23.

26. Tris(3,5-di-tert-butyl-4-trimethylsilyloxy)-phosphine according to claim 23.

27. Bis(3,5-di-tert-butyl-4-hydroxyphenyl)-phenylphosphine according to claim 23.

28. Tris(3,5-di-tert-butyl-4-hydroxyphenyl)-phosphine according to claim 23.

* * * * *